(12) United States Patent
Amari et al.

(10) Patent No.: US 11,229,583 B2
(45) Date of Patent: Jan. 25, 2022

(54) MULTILAYER NANOFIBER SHEET AND ADHESION METHOD FOR SAME

(71) Applicant: Kao Corporation, Tokyo (JP)

(72) Inventors: Naomi Amari, Ichikai-machi (JP); Takahiro Hirano, Utsunomiya (JP)

(73) Assignee: KAO CORPORATION, Tokyo (JP)

( * ) Notice: Subject to any disclaimer, the term of this patent is extended or adjusted under 35 U.S.C. 154(b) by 77 days.

(21) Appl. No.: 16/465,057

(22) PCT Filed: Nov. 29, 2017

(86) PCT No.: PCT/JP2017/042831
§ 371 (c)(1),
(2) Date: May 29, 2019

(87) PCT Pub. No.: WO2018/101336
PCT Pub. Date: Jun. 7, 2018

(65) Prior Publication Data
US 2019/0282460 A1   Sep. 19, 2019

(30) Foreign Application Priority Data

Nov. 30, 2016   (JP) .............................. JP2016-233559

(51) Int. Cl.
*A61K 8/02*   (2006.01)
*B32B 5/02*   (2006.01)
(Continued)

(52) U.S. Cl.
CPC .............. *A61K 8/0208* (2013.01); *A61K 8/02* (2013.01); *A61K 8/72* (2013.01); *A61K 8/73* (2013.01);
(Continued)

(58) Field of Classification Search
CPC .......... A61K 8/0208; A61K 8/73; A61K 8/81; A61K 8/85; A61K 8/02; A61K 8/72;
(Continued)

(56) References Cited

U.S. PATENT DOCUMENTS

2006/0020235 A1* 1/2006 Siniaguine .............. A61F 15/02
602/41
2007/0020320 A1* 1/2007 David .................... A61K 33/00
424/445

(Continued)

FOREIGN PATENT DOCUMENTS

CN   102245378 A   11/2011
CN   102256782 A   11/2011
(Continued)

OTHER PUBLICATIONS

International Search Report (PCT/ISA/210) issued in PCT/JP2017/042831, dated Feb. 27, 2018.
(Continued)

*Primary Examiner* — Jennifer A Steele
(74) *Attorney, Agent, or Firm* — Birch, Stewart, Kolasch & Birch, LLP.

(57) ABSTRACT

A multilayer nanofiber sheet (10) includes: a nanofiber layer (11) including nanofibers which comprise a water-soluble polymer compound; a substrate layer (12) arranged on one surface side of the nanofiber layer (11); and a water-insoluble porous layer (13) arranged on the other surface side of the nanofiber layer (11). The three layers are layered,
(Continued)

and the multilayer nanofiber sheet is used in a state in which a surface thereof on the porous layer side is arranged so as to face a surface of an object. Preferably, the three layers are layered in a fixed state. Preferably, the porous layer (13) has a thickness of from 3 to 1000 μm.

20 Claims, 1 Drawing Sheet

(51) Int. Cl.
| | |
|---|---|
| *B32B 5/26* | (2006.01) |
| *B32B 27/12* | (2006.01) |
| *D04H 1/4374* | (2012.01) |
| *D04H 1/593* | (2012.01) |
| *D04H 1/4382* | (2012.01) |
| *A61K 8/73* | (2006.01) |
| *A61K 8/81* | (2006.01) |
| *A61K 8/72* | (2006.01) |
| *B32B 5/24* | (2006.01) |
| *A61K 8/85* | (2006.01) |
| *A61Q 19/00* | (2006.01) |
| *D04H 1/728* | (2012.01) |

(52) U.S. Cl.
CPC .................. *A61K 8/81* (2013.01); *B32B 5/02* (2013.01); *B32B 5/022* (2013.01); *B32B 5/24* (2013.01); *B32B 5/26* (2013.01); *B32B 27/12* (2013.01); *D04H 1/4374* (2013.01); *D04H 1/43828* (2020.05); *D04H 1/43835* (2020.05); *D04H 1/43838* (2020.05); *D04H 1/593* (2013.01); *A61K 8/85* (2013.01); *A61Q 19/00* (2013.01); *D04H 1/728* (2013.01)

(58) Field of Classification Search
CPC .......... A61Q 19/00; B32B 5/022; B32B 5/26; B32B 27/12; B32B 5/02; B32B 5/24; D04H 1/4374; D04H 1/593; D04H 1/4382; D04H 1/728; A61F 13/00; A61L 15/00
See application file for complete search history.

(56) References Cited

U.S. PATENT DOCUMENTS

| | | | |
|---|---|---|---|
| 2007/0134304 A1* | 6/2007 | Aubrun-Sonneville | ..................... A61K 8/8111 424/443 |
| 2009/0075354 A1* | 3/2009 | Reneker | ................. D04H 1/407 435/182 |
| 2010/0150976 A1* | 6/2010 | Schnitzler | ............ A61K 8/0208 424/401 |
| 2011/0256397 A1 | 10/2011 | Tojo et al. | |
| 2011/0259518 A1* | 10/2011 | Tojo | ........................ D04H 1/559 156/308.6 |
| 2013/0142852 A1* | 6/2013 | Tojo | ........................ A61K 9/70 424/401 |
| 2017/0136157 A1* | 5/2017 | Sato | ........................ A61L 31/10 |
| 2017/0251789 A1 | 9/2017 | Kim et al. | |

FOREIGN PATENT DOCUMENTS

| | | | | |
|---|---|---|---|---|
| JP | 2008-179629 A | | 8/2008 | |
| JP | 2012-12317 A | | 1/2012 | |
| JP | 2013-119676 A | | 6/2013 | |
| JP | 2014-152160 A | | 8/2014 | |
| JP | 2014152160 A | * | 8/2014 | ............. A61K 8/027 |
| JP | 2015-17346 A | | 1/2015 | |
| JP | 2015-189224 A | | 11/2015 | |
| WO | WO 2012/002390 A1 | | 1/2012 | |
| WO | WO 2014/125407 A1 | | 8/2014 | |
| WO | WO 2015/152204 A1 | | 10/2015 | |
| WO | WO 2016/032297 A1 | | 3/2016 | |

OTHER PUBLICATIONS

U.S. Appl. No. 13/807,626, filed Feb. 19, 2013.
Extended European Search Report dated May 29, 2020 for Application No. 17876660.6.

* cited by examiner

MULTILAYER NANOFIBER SHEET AND ADHESION METHOD FOR SAME

TECHNICAL FIELD

The present invention relates to a multilayer nanofiber sheet. The present invention also relates to an adhesion method for a multilayer nanofiber sheet.

BACKGROUND ART

Nanofibers are applied, for example, in fields that require optical characteristics, such as high transparency, employing nanosize effects. For example, a transparent fabric can be achieved by setting the diameter of the nanofibers to a dimension less than or equal to visible wavelengths. Further, structural coloring can be achieved by setting the diameter of the nanofibers to a dimension equivalent to visible wavelengths. Application of nanofibers is also being studied in fields that require high adsorption characteristics and high surface activity by employing super-specific surface area effects, and in fields that require dynamic characteristics, such as tensile strength, and electric characteristics, such as high electric conduction, by employing supramolecular alignment effects. With such characteristics, nanofibers are used, for example, as monofilaments and also for aggregates (fabrics) and composite materials.

A proposed application example of nanofibers is a cosmetic sheet in which a cosmetic or a cosmetic component is retained in a mesh structure made of polymer-compound nanofibers (see Patent Literature 1). The Patent Literature describes that the cosmetic sheet can be improved in terms of adhesiveness and the feel during attachment to the face, hands, and feet, and can also be improved in terms of storability.

Another known technique, other than the aforementioned techniques, for sheets including nanofibers produced by electrostatic spinning is a technique for producing multilayer nanofiber sheets by layering a layer including nanofibers onto another layer. For example, Patent Literature 2 discloses a cosmetic sheet including: a substrate sheet; a nanofiber sheet peelably provided on a surface of the substrate sheet; and a cover sheet provided on a surface of the nanofiber sheet. The Patent Literature describes that, with this cosmetic sheet, when the nanofiber sheet is attached to the skin by holding the substrate sheet with the hand, the nanofiber sheet easily peels off from the surface of the substrate sheet and adheres to the skin.

Patent Literature 3 discloses a layered sheet including: a contact layer made of a nanofiber nonwoven fabric; a support layer made of a fibrous porous substance; and a connection layer that connects the two layers and that is made of a nanofiber nonwoven fabric. In this layered sheet, the contact layer made of a nanofiber nonwoven fabric has a soft texture and low tensile strength, whereas the support layer made of a fibrous porous substance is somewhat stiff but has high tensile strength, and the two layers are connected by the connection layer. The Patent Literature thus describes that the layered sheet, as a whole, is highly flexible but firm, and the surface of the contact layer has a soft texture and smooth texture to the touch.

CITATION LIST

Patent Literature

Patent Literature 1: JP 2008-179629A
Patent Literature 2: JP 2014-152160A
Patent Literature 3: JP 2015-189224A

SUMMARY OF INVENTION

The present invention provides a multilayer nanofiber sheet including: a nanofiber layer including nanofibers which comprise a water-soluble polymer compound; a substrate layer arranged on one surface side of the nanofiber layer; and a water-insoluble porous layer arranged on the other surface side of the nanofiber layer. The three layers are layered, and the multilayer nanofiber sheet is used in a state in which a surface thereof on the porous layer side is arranged so as to face a surface of an object.

The present invention also provides a multilayer nanofiber sheet adhesion method for making the aforementioned multilayer nanofiber sheet adhere to a surface of an object, the method involving bringing a surface of the multilayer nanofiber sheet on the porous layer side into contact with a surface of an object in a state where the multilayer nanofiber sheet's surface on the porous layer side is moistening with a liquid substance, and thus making the multilayer nanofiber sheet's surface adhere to the object's surface.

The present invention also provides a multilayer nanofiber sheet adhesion method for making the aforementioned multilayer nanofiber sheet adhere to a surface of an object, the method involving bringing a surface of the multilayer nanofiber sheet on the porous layer into contact with a surface of an object in a state where the object's surface is moistened with a liquid substance, and thus making the multilayer nanofiber sheet's surface adhere to the object's surface.

The present invention also provides a multilayer nanofiber sheet adhesion method for making the aforementioned multilayer nanofiber sheet adhere to a surface of an object, the method involving: bringing a surface of the multilayer nanofiber sheet on the porous layer side into contact with a surface of an object in a state where the multilayer nanofiber sheet's surface on the porous layer side is moistening with a liquid substance, and thus making the multilayer nanofiber sheet's surface adhere to the object's surface; and then peeling off the substrate layer from the nanofiber layer.

The present invention also provides a multilayer nanofiber sheet adhesion method for making the aforementioned multilayer nanofiber sheet adhere to a surface of an object, the method involving: bringing a surface of the multilayer nanofiber sheet on the porous layer into contact with a surface of an object in a state where the object's surface is moistened with a liquid substance, and thus making the multilayer nanofiber sheet's surface adhere to the object's surface; and then peeling off the substrate layer from the nanofiber layer.

DESCRIPTION OF EMBODIMENTS

The sheet made of nanofibers as disclosed in Patent Literature 1 has low rigidity (i.e., is not so firm) due to the extreme fineness of the nanofibers, and thus does not have good handleability.

In the cosmetic sheet disclosed in Patent Literature 2, the nanofiber sheet and the substrate sheet which constitute the cosmetic sheet are layered in a peelable manner. Thus, the nanofiber sheet may inadvertently peel off from the substrate sheet while attaching the cosmetic sheet to the skin. Thus, the cosmetic sheet does not necessarily have good handleability.

In the layered sheet disclosed in Patent Literature 3, the layers constituting the sheet are connected and integrated by heating and fusion bonding, and thus, there is no possibility that the layers will peel apart, in contrast to the cosmetic sheet disclosed in Patent Literature 2. However, in cases where the nanofibers constituting the contact layer, which comes into contact with the target surface, is made of a water-soluble material, the nanofibers may dissolve due to moisture etc. on the fingertips. Thus, the layered sheet does not necessarily have good handleability.

The present invention relates to an improvement in multilayer sheets including a nanofiber layer, and more specifically, to a multilayer nanofiber sheet having excellent handleability and high adhesiveness to an object.

Figure 1:
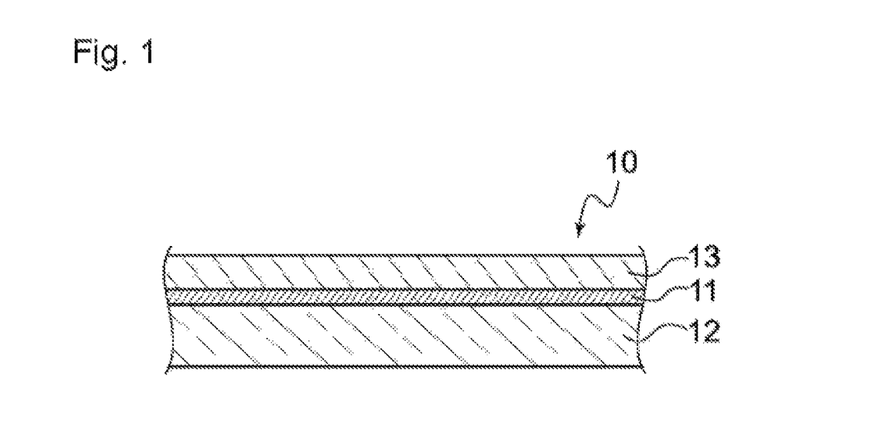
FIG. 1 is a cross-sectional view, along the thickness direction, schematically illustrating a structure of an embodiment of a multilayer nanofiber sheet of the invention.

The present invention is described below according to preferred embodiments thereof with reference to the drawings. FIG. 1 is a cross-sectional view, along the thickness direction, schematically illustrating a structure of an embodiment of a multilayer nanofiber sheet of the invention. As illustrated in the figure, the multilayer nanofiber sheet 10 of the present embodiment comprises a nanofiber layer 11 including nanofibers. A substrate layer 12 is arranged on one surface side of the nanofiber layer 11. A porous layer 13 is arranged on the other surface side of the nanofiber layer 11. The nanofiber layer 11 and the substrate layer 12 are in direct contact with one another, and there is no other layer between the two layers. Similarly, the nanofiber layer 11 and the porous layer 13 are in direct contact with one another, and there is no other layer between the two layers. This, however, does not preclude interposing one or more other layers between the nanofiber layer 11 and the substrate layer 12. Similarly, this does not preclude interposing one or more other layers between the nanofiber layer 11 and the porous layer 13.

In the multilayer nanofiber sheet 10 of the present embodiment as illustrated in FIG. 1, the outer surface of the substrate layer 12 and the outer surface of the porous layer 13 respectively constitute the outer surfaces of the multilayer nanofiber sheet 10. Instead, depending on the concrete usage of the multilayer nanofiber sheet 10, one or more other layers may be layered on the outer surface of the substrate layer 12 and/or the outer surface of the porous layer 13.

The nanofiber layer 11 in the multilayer nanofiber sheet 10 is a layer including nanofibers. Herein, "nanofibers" typically have a thickness of from 10 to 3000 nm, more preferably from 10 to 1000 nm, in terms of equivalent circle diameter. The thickness of the nanofiber can be measured, for example, with a scanning electron microscope (SEM) by: observing the fibers at a magnification of 10000×; discretionarily choosing, from the two-dimensional image, 10 pieces of fibers, excluding defected fibers (clumps of nanofibers, intersecting sections of nanofibers, and polymer liquid droplets); and directly reading the fiber diameter along a line orthogonal to the length direction of each fiber.

The nanofiber layer 11 may be constituted only by the nanofibers, or may include other structural materials in addition to the nanofibers. Examples of other structural materials include particles and fibers other than nanofibers. In cases where the nanofiber layer 11 includes other structural materials in addition to nanofibers, the mass of the nanofibers within the nanofiber layer 11 is preferably from 1 to 100 mass %.

The nanofiber layer 11 may include one or more types of nanofibers. In cases where the nanofiber layer 11 includes only one type of nanofibers, the nanofibers that are used include a water-soluble polymer compound. In cases where the nanofiber layer 11 includes two or more types of nanofibers, at least one type of nanofibers includes a water-soluble polymer compound. In some cases, the nanofiber layer 11 may include at least: first nanofibers including a first water-soluble polymer compound; and second nanofibers including a second water-soluble polymer compound. By including, in the nanofiber layer 11, at least nanofibers including a water-soluble polymer compound, the nanofiber layer 11 becomes water-soluble as a whole.

Herein, a "water-soluble polymer compound" has a property wherein, in an environment of 1 atm. and 23° C., when 1 g of the water-soluble polymer compound is immersed in 10 g of ion-exchanged water, at least 0.5 g of the immersed water-soluble polymer compound dissolves into water—more preferably, at least 0.8 g of the immersed water-soluble polymer compound dissolves into water—after 24 hours.

Either a natural polymer or a synthetic polymer may be used as the water-soluble polymer compound. Examples of natural polymers include pullulan, mucopolysaccharides such as hyaluronic acid, chondroitin sulfate, poly-γ-glutamic acid, modified corn starch, β-glucan, glucooligosaccharide, heparin, and keratosulfate, pectin, xylan, lignin, glucomannan, galacturonic acid, psyllium seed gum, tamarind seed gum, gum arabic, tragacanth gum, water-soluble soybean polysaccharides, alginic acid, carrageenan, laminaran, agar (agarose), fucoidan, and methyl cellulose. Examples of synthetic polymers include partially saponified polyvinyl alcohol, low-saponification polyvinyl alcohol, polyvinyl pyrrolidone, polyethylene oxide, and sodium polyacrylate. One type of the water-soluble polymer compound may be used singly, or two or more types may be used in combination. Among the aforementioned water-soluble polymer compounds, from the viewpoint of facilitating preparation of nanofibers, it is preferable to use a natural polymer such as pullulan, or a synthetic polymer such as partially saponified polyvinyl alcohol, low-saponification polyvinyl alcohol, polyvinyl pyrrolidone, or polyethylene oxide.

The percentage of the water-soluble polymer compound(s) included in the nanofibers is preferably 20 mass % or greater, more preferably 40 mass % or greater. There is no particular upper limit value, and the percentage of the water-soluble polymer compound(s) with respect to composite nanofibers may be 100 mass %. Setting the percentage of the water-soluble polymer compound(s) within this range is preferable, as this allows the composite nanofibers to successfully dissolve into water, and facilitates preparation of the nanofibers.

In cases where the nanofibers include a water-soluble polymer compound, the nanofibers may further include other components. Examples of other components include medicinal components, moisturizing components, various vitamins, perfumes, anti-UV agents, surfactants, coloring pigments, body pigments, dyes, stabilizers, antiseptics, and antioxidants. One of the aforementioned components may be used singly, or two or more types may be included in a single nanofiber in combination. Further, it is possible to include a first component included in first nanofibers and to include a second component in second nanofibers. In this case, the first component and the second component may respectively be an acid component and a carbonate, for example. By employing such components, the multilayer nanofiber sheet 10 can generate carbon dioxide. In this case, the water-soluble polymer compound constituting the first nanofibers may be the same type as, or a different type from, the water-soluble polymer compound constituting the second nanofibers.

In cases of including other components in the nanofibers, there is no particular limitation, so long as the other components are included in a state where they can elute into water. An example of a method for including other components in the nanofibers is to prepare the nanofibers by completely dissolving the nanofibers and the other components in water and mixing the same in this state, to include the other components in the nanofibers. Further, in cases where the water-soluble polymer compound-containing nanofibers have hollow sections in a portion thereof, the other components may be emulsified and be contained in the hollow sections. Depending on the type of reaction of the other component(s), a single type of component may be included in the nanofibers, or two or more components may be included.

Regardless of the form in which the nanofibers include the other component(s), the percentage of the other component(s) included in the nanofibers is preferably 5 mass % or greater, more preferably 10 mass % or greater, and the upper limit value is preferably 80 mass % or less, more preferably 75 mass % or less. By setting the percentage of the other component(s) to 80 mass % or less, nanofibers can be formed successfully.

In cases where the nanofiber layer 11 includes two types of components, i.e., the first component and the second component, it is preferable that the nanofiber layer 11 is constituted by first nanofibers including the first component (referred to hereinafter also as "first composite nanofibers") and second nanofibers including the second component (referred to hereinafter also as "second composite nanofibers"). In this case, in the first composite nanofibers, the first component is carried by the first nanofibers by means of a first water-soluble polymer compound, and no second component is included. Further, in the second composite nanofibers, the second component, which is capable of undergoing a chemical reaction with the first component, is carried by the second nanofibers by means of a second water-soluble polymer compound, and no first component is included. Note that the first water-soluble polymer compound constituting the first nanofibers may be the same type as, or a different type from, the second water-soluble polymer compound constituting the second nanofibers.

The nanofiber layer 11 may be formed as a single layer by mixing the first composite nanofibers and the second composite nanofibers (this state is referred to hereinafter as "mixed type"). Alternatively, the nanofiber layer 11 may have a layered structure, and the layers may include the respective composite nanofibers (this state is referred to hereinafter as "layered type").

In cases where the nanofiber layer 11 has a layered structure, it is preferable that one layer includes one type of composite nanofibers, and does not include the other type of composite nanofibers. More specifically, the nanofiber layer 11 may have a layered structure including: a first layer including the first composite nanofibers but not including the second composite nanofibers; and a second layer including the second composite nanofibers but not including the first composite nanofibers. When comparing the layered-type nanofiber layer 11 with the mixed-type nanofiber layer 11, the mixed type is preferable in that the reactivity between the components tends to be higher because the components included in the respective nanofibers exist closer to one another. Note that one type of product may be produced by the reaction between the first component and the second component, or two or more types of products may be produced.

The basis weight of the nanofiber layer 11 is preferably 0.01 $g/m^2$ or greater, more preferably 0.1 $g/m^2$ or greater, and preferably 100 $g/m^2$ or less, more preferably 50 $g/m^2$ or less. More specifically, the basis weight of the nanofiber layer 11 is preferably from 0.01 to 100 $g/m^2$, more preferably from 0.1 to 50 $g/m^2$. When the nanofiber layer 11 has a basis weight within the aforementioned range, adhesiveness between the multilayer nanofiber sheet 10 and an object becomes favorable. The basis weight of the nanofiber layer 11 can be measured, for example, by cutting out a 50-by-50 mm sheet, weighing the mass of the sheet with a scale, and calculating the basis weight by dividing the mass by the sheet's area.

The substrate layer 12 arranged on one surface of the nanofiber layer 11 is used for improving the handleability of the multilayer nanofiber sheet 10. For this purpose, it is preferable that the substrate layer 12 has a moderate rigidity. From this viewpoint, it is preferable that the Taber stiffness of the substrate layer is preferably 0.01 mN·m or greater, more preferably 0.02 mN·m or greater, and preferably 0.4 mN·m or less, more preferably 0.3 mN·m or less, and more specifically, preferably from 0.01 to 0.4 mN·m, more preferably from 0.02 to 0.3 mN·m. The Taber stiffness is measured by the "Taber stiffness testing method" as stipulated by JIS P8125-2000.

Preferably, the substrate layer 12 is water-insoluble. Herein, "water-insoluble" refers to a property wherein, in an environment of 1 atm. and 23° C., when 1 g of the substrate layer is immersed in 10 g of ion-exchanged water, more than 0.5 g of the immersed substrate layer 12 remains undissolved—more preferably, more than 0.8 g remains undissolved—after 24 hours. Stated differently, "water-insoluble" refers to a property wherein, in an environment of 1 atm. and 23° C., when 1 g of the substrate layer is immersed in 10 g of ion-exchanged water, less than 0.5 g of the immersed substrate layer 12 dissolves more preferably, less than 0.2 g dissolves after 24 hours. From this viewpoint, it is preferable that the substrate layer 12 is constituted by a water-insoluble polymer compound.

Examples of the water-insoluble polymer compound include polyolefin resins, polyethylene terephthalate resins, polybutylene terephthalate resins, polylactic acid (PLA), polyacrylonitrile resins, acrylic resins such as polymethacrylate resins, polystyrene resins, polyvinyl butyral resins, polyurethane resins, polyamide resins, polyimide resins, and polyamide imide resins. The water-insoluble polymer compound may be used singly, or two or more types may be used in combination.

The form of the substrate layer 12 is not particularly limited, and, for example, a film form or a fiber aggregate form may be employed. Preferably, the substrate layer 12 has low air permeability, and from this viewpoint, it is preferable that the substrate layer 12 is in the form of a film. When expressing the air permeability of the substrate layer 12 in air resistance (Gurely; JIS P8117:2009), it is preferable that the value is 30 s/100 ml or greater. Making the substrate layer 12's air permeability low is advantageous, in terms that, when the multilayer nanofiber sheet 10 is attached to the skin for example, the sealability of the skin is improved, and effective components included in the nanofiber layer 11 and effective components included in a liquid substance used for attaching the multilayer nanofiber sheet 10 can penetrate into the skin effectively.

In cases where the substrate layer 12 is in a film form, the thickness is preferably 5 µm or greater, more preferably 10 µm or greater, and preferably 500 µm or less, more preferably 300 µm or less, and more specifically, preferably from 5 to 500 µm, more preferably from 10 to 300 µm. The thickness of the substrate layer 12 is measured with Super Litematic VL-50AH from Mitutoyo Corporation, in a state where a load of 0.01 N is applied. Measurement is performed at five points in a 50-by-50 mm region, and the average value is considered the thickness. In the description below, "thickness" refers to the value measured according to this method.

It is advantageous that the substrate layer 12 is in the form of a transparent or translucent film, in terms that, when the multilayer nanofiber sheet 10 is attached to the skin by using a liquid substance, it is possible to visually observe the state of the skin where the sheet is attached and/or the state of dissolution of the nanofiber layer 11 through the substrate layer 12. Further, the change in the state of the skin and/or the change in the state of dissolution of the nanofiber layer 11 may serve as a sign to provide the user with a sense of effectiveness.

The porous layer 13, which is arranged on the opposite side from the substrate layer 12 across the nanofiber layer 11, is a layer that is porous and has a multitude of pores. Herein, "porous" refers to a liquid-permeable structure through which a liquid can permeate. The pores of the porous layer 13 preferably have an open-cell structure. For example, the porous layer 13 may be in the form of a fiber aggregate layer, or a spongy layer having an open-cell structure.

In cases where the porous layer 13 is made of a fiber aggregate layer, nanofibers may be used as the fibers constituting the fiber aggregate. Alternatively, fibers thicker than nanofibers may be used. Alternatively, the porous layer 13 may be made by employing nanofibers and fibers thicker than nanofibers in combination. Particularly, any of various types of nonwoven fabrics or mesh sheets may be particularly preferable as the fiber aggregate layer employed for the porous layer 13. Examples of nonwoven fabrics that may be used include, but are not limited to, melt-blown nonwoven fabrics, spun-bonded nonwoven fabrics, air-through nonwoven fabrics, and spun-laced nonwoven fabrics. The thickness of the fibers or strands that constitute the nonwoven fabric or mesh sheet may be in the order of nanofibers, or may be thicker.

Regardless of the form of the porous layer 13, it is advantageous that the porous layer 13 is water-insoluble. This is because, when the porous layer 13 is water-insoluble, the porous layer 13 can be prevented from dissolving when the multilayer nanofiber sheet 10 is attached to the skin by using a liquid substance. So, in cases where the porous layer 13 is, for example, a fiber aggregate layer, the fibers, e.g., nanofibers, constituting the fiber aggregate are preferably water-insoluble. The definition of "water-insoluble" is as described above. From this viewpoint, it is preferable that the porous layer 13 is constituted by a water-insoluble polymer compound.

Examples of the water-insoluble polymer compound include polyolefin resins, polyethylene terephthalate resins, polybutylene terephthalate resins, polylactic acid (PLA), polyacrylonitrile resins, acrylic resins such as polymethacrylate resins, polystyrene resins, polyvinyl butyral resins, polyurethane resins, polyamide resins, polyimide resins, and polyamide imide resins. The water-insoluble polymer compound may be used singly, or two or more types may be used in combination.

The thickness of the porous layer 13 is preferably 3 µm or greater, more preferably 5 µm or greater, even more preferably 10 µm or greater. The thickness of the porous layer 13 is preferably 1000 µm or less, more preferably 500 µm or less, even more preferably 450 µm or less. More specifically, the thickness of the porous layer 13 is preferably from 3 to 1000 µm, more preferably from 5 to 500 µm, even more preferably from 10 to 450 µm. By setting the thickness of the porous layer 13 within the aforementioned range, it is possible to effectively prevent disadvantages such as: inadvertent dissolution of the nanofiber layer 11 due to moisture on the fingertips; migration of the dissolved solution of the nanofiber layer 11 onto the skin in large amounts; the resultant stickiness on the skin which thereby impairs the feel upon use; and large amounts of dried products of the water-soluble polymer compound, which constitutes the nanofibers, remaining on the skin as flakes which thereby impairs the feel upon use. There are also advantages in that effective components included in the dissolved solution of the nanofiber layer 11 can easily reach the skin through the porous layer 13 and the effective components can penetrate easily into the skin.

As described above, in the multilayer nanofiber sheet 10 illustrated in FIG. 1, the nanofiber layer 11, the substrate layer 12, and the porous layer 13 are layered. The multilayer nanofiber sheet 10 may be bound together to an extent that the layers can separate when the sheet 10 is held with the fingers and subjected to an external force of a degree at which the sheet is bent or rubbed with the fingers. Stated differently, the layers may be layered in a peelable state.

In the multilayer nanofiber sheet 10, one of the layers constituting the multilayer nanofiber sheet 10 may be peelable, or each of the layers may be peelable independently. More specifically, the nanofiber layer 11 and the porous layer 13 may be peelable from the substrate layer 12, or the nanofiber layer 11 and the substrate layer 12 may be peelable from the porous layer 13, or each of the layers may be peelable independently. Peelable layers can be formed by layering the layers such that a force, such as Van der Waals force or electrostatic force, is effected between the layer to be peeled off and the non-peeled layer, or by subjecting the peeled layer's surface that opposes the non-peeled layer to a peelable treatment such as application of a silicone resin or a corona discharge treatment.

From the viewpoint of improving handleability, in the multilayer nanofiber sheet 10, it is preferable that the nanofiber layer 11, the substrate layer 12, and the porous layer 13 are layered in a fixed state. Herein, "fixed" refers to a state wherein, even when the multilayer nanofiber sheet 10 is held with the fingers and the sheet 10 is bent or rubbed with the fingers, the three layers are bound together to an extent that the layers do not separate and an integrated state is maintained. Stated differently, "fixed" means that the layers are layered in a non-peelable state. Note, however, that the definition of "fixed" as used herein is based on the assumption that the external force applied to the multilayer nanofiber sheet 10 is of an extent of force that arises when the sheet is touched in a normal way, and does not take into consideration strong external forces applied intentionally to cause the layers to peel apart.

The fixed state of the three layers constituting the multilayer nanofiber sheet 10 is maintained (a) before use of the multilayer nanofiber sheet 10, and (b) after the multilayer nanofiber sheet 10 has been moistened with a liquid substance and the nanofiber layer 11 has dissolved. In the case (b), the nanofiber layer 11 in the multilayer nanofiber sheet 10 may have dissolved, and so in this case, it is preferable that the substrate layer 12 and the porous layer 13 are fixed together, but they may be fixed by a force, such as Van der Waals force, adhesive force, or liquid surface tension, by means of the nanofiber layer 11 dissolved by the liquid substance.

Fixing of the three layers of the multilayer nanofiber sheet 10 may be achieved, for example, by adhesion using an adhesive, compression bonding, joining by ultrasonic sealing, laser fusion bonding, or thermal fusion bonding by heat sealing. The fixing pattern is not particularly limited, and it is possible to employ, for example, a linear fixing pattern, a dotted fixing pattern, or a fixing pattern which is a combination thereof. In cases of performing fixing by applying heat, the porous layer 13 may melt by the heat, which may cause the pores to close and the structure to deform; thus, it is advantageous to employ a method wherein it is possible to minimize the area in which heat is applied during fixing.

The position for fixing the three layers in the multilayer nanofiber sheet 10 may, for example, be continuous (filled solidly) over the entire surface of the multilayer nanofiber sheet 10. However, from the viewpoint of maximizing the features of the nanofiber layer 11, it is preferable that the layers are fixed by the smallest area possible. For this purpose, it is preferable that the fixing positions are formed discontinuously on the surface of the nanofiber sheet 10. For example, from the viewpoint of providing the sheet with softness and a pleasant feel to the touch and efficiently employing the effective components integrated in the nanofiber sheet 10, it is advantageous that the fixing positions are configured such that the fixing points are formed in a scattered and distributed manner on the multilayer nanofiber sheet 10, or are configured such that the fixing points are formed only along the peripheral edges.

The degree of fixing of the multilayer nanofiber sheet 10 can be evaluated on the basis of peeling strength. Peeling strength is defined as the strength for peeling at least one layer among the plurality of layers constituting the multilayer nanofiber sheet 10. A "fixed state" refers to a case where the peeling strength is 0.01 N or greater. A "peelable state" refers to a case where the peeling strength is less than 0.01 N. A concrete method for measuring the peeling strength is described in detail further below in the Examples.

The multilayer nanofiber sheet 10 is used, for example, by adhering to an object. For example, the multilayer nanofiber sheet 10 can be used by being attached to the skin, teeth, gums, or hair of a human being, the skin, teeth, or gums of a non-human mammal, or the surface of a plant such as the branches or leaves. In this case, the surface of the multilayer nanofiber sheet 10 on the porous layer 13 side is made to face the surface of an object.

Before bringing the multilayer nanofiber sheet 10 into contact with the surface of an object and causing adhesion, the surface of the object may be moistened with a liquid substance such as water or an aqueous liquid, such as water including a water-soluble organic solvent. In this way, the action of surface tension can be employed to cause the multilayer nanofiber sheet 10 to successfully adhere to the surface of the object. Further, the nanofiber layer 11 of the multilayer nanofiber sheet 10 can be made to successfully dissolve into the liquid substance.

In order to moisten the surface of an object, for example, the liquid substance made of one of various aqueous liquids may simply be applied or sprayed onto the surface. The liquid substance that is used for application or spraying is a substance that includes a liquid component at the temperature at which the multilayer nanofiber sheet 10 is attached and that has a viscosity (viscosity measured with an E-type viscometer) of around 5000 mPa·s or less at that temperature. Examples of such a liquid substance include water, aqueous solutions, and aqueous dispersions. For the liquid substance, it is also possible to use, for example, emulsions such as O/W emulsions, or aqueous liquids thickened by various thickeners such as thickening polysaccharides. Instead of moistening the surface of the object, the surface of the multilayer nanofiber sheet 10 on the porous layer 13 side may be moistened with a liquid substance.

Both in cases where the surface of the object is moistened and where the surface of the multilayer nanofiber sheet 10 on the porous layer 13 side is moistened, when the multilayer nanofiber sheet 10 is placed in contact with and attached to an object, the liquid substance comes into contact with the nanofiber layer 11 through the porous layer 13, and the nanofibers constituting the nanofiber layer 11 dissolve into the liquid substance. The dissolved solution produced thereby is supplied to the surface of the object through the porous layer 13. As a result, adhesiveness of the multilayer nanofiber sheet 10 to the object is achieved through the porous layer 13.

The aforementioned dissolved solution includes effective components included in the nanofibers and effective components included in the liquid substance. Thus, supplying the dissolved solution to the surface of the object means that the effective components included therein are also supplied to the surface of the object. As a result, in cases where the object is the human skin, for example, the effective components effectively penetrate into the skin. Further, in the multilayer nanofiber sheet 10, the dissolved solution is supplied to the surface of the object through the porous layer 13. Thus, the porous layer inhibits excessive distribution of the dissolved solution, and effectively prevents an excessive amount of the dissolved solution from being supplied to the surface of the object. It is thus possible to reduce stickiness caused by the dissolved solution remaining on the skin, as well as the filmy feel caused by drying of the dissolved solution.

Particularly, since the multilayer nanofiber sheet 10 of the invention includes the porous layer 13, the sheet 10 can adhere to the human skin etc. for a long time with high adhesiveness, without causing an uncomfortable feel. Thus, the present invention is capable of letting effective components penetrate sustainably into the section where the sheet is attached, and is also capable of achieving moisturizing effects due to the attachment of the sheet.

In cases where any of the layers layered in the multilayer nanofiber sheet 10 is not fixed and is peelable, the layer to be peeled can be peeled off and removed after bringing the multilayer nanofiber sheet 10 into contact with the surface of an object and making the sheet adhere thereto. In the multilayer nanofiber sheet 10, in cases where, for example, the substrate layer 12 is the layer to be peeled and the multilayer nanofiber sheet is configured so that the substrate layer 12 is peeled off from the nanofiber layer 11, the multilayer nanofiber sheet 10 is prepared as described further below so that the nanofiber layer 11 and the substrate layer 12 are not fixed but the nanofiber layer 11 and the porous layer 13 are fixed. Then, after bringing the prepared multilayer nanofiber sheet 10 into contact with the surface of an object and making the sheet adhere thereto, an external force is applied to the substrate layer 12 to peel off and remove the substrate layer 12 from the nanofiber layer 11. The surface of the object after peeling and removal of the substrate layer 12 is in a state where the sheet, in which the nanofiber layer 11 and the porous layer 13 are layered, is adhering thereto. Thus, the aforementioned effects by the porous layer 13 and the effective components included in the nanofiber layer 11 are sufficiently achieved.

For an embodiment in which the object is the human skin, it is possible to use, for example, a multilayer nanofiber sheet 10 including a nanofiber layer 11 employing nanofibers that includes a water-soluble polymer compound and in which an acid component and a carbonate, serving as other components, are integrated. In this case, it is possible to produce, as an effective component, carbon dioxide through a chemical reaction. By employing the blood circulation-improving effect and metabolism-improving effect of carbon dioxide, it is possible to achieve effects with aesthetic purposes (not medical purposes), such as whitening and beautifying of the skin, in the section where the sheet 10 is attached.

In the multilayer nanofiber sheet 10, in cases where the substrate layer 12 is peelable, it is possible to employ a method wherein, for example, the multilayer nanofiber sheet 10 is attached to the skin to produce carbon dioxide without peeling/removing the substrate layer 12 during production of carbon dioxide, and then the substrate layer 12 is peeled and removed once production is finished. In this adhesion method, sealing by the substrate layer 12 enables sufficient achievement of aesthetic and moisturizing effects in the section where the sheet 10 is attached.

An example of a combination of a first component and a second component for producing carbon dioxide includes the use of an acid component as the first component and a carbonate as the second component. Further, from the viewpoint of improving reactivity, it is more preferable that that the nanofiber layer 11 is configured as the aforementioned mixed type.

Examples of acid components used for producing carbon dioxide include water-soluble organic acids and inorganic acids. Examples of such organic acids include: dicarboxylic acids such as oxalic acid, malonic acid, succinic acid, glutaric acid, adipic acid, pimelic acid, fumaric acid, maleic acid, phthalic acid, isophthalic acid, and terephthalic acid; acidic amino acids such as glutamic acid and aspartic acid; and oxyacids such as glycolic acid, malic acid, tartaric acid, itatartaric acid, citric acid, isocitric acid, lactic acid, hydroxyacrylic acid, α-oxybutyric acid, glyceric acid, tartronic acid, salicylic acid, gallic acid, tropic acid, ascorbic acid, and gluconic acid. One or more types of the above may be used.

Examples of inorganic acids include phosphoric acid, potassium dihydrogen phosphate, sodium dihydrogen phosphate, sodium sulfite, potassium sulfite, sodium pyrosulfite, potassium pyrosulfite, sodium acid hexametaphosphate, potassium acid hexametaphosphate, sodium acid pyrophosphate, potassium acid pyrophosphate, and sulfamic acid. One or more types of the above may be used.

Examples of carbonates include ammonium carbonate, ammonium bicarbonate, potassium carbonate, potassium bicarbonate, potassium sesquicarbonate, sodium carbonate, sodium bicarbonate, sodium sesquicarbonate, lithium carbonate, lithium bicarbonate, lithium sesquicarbonate, cesium carbonate, cesium bicarbonate, cesium sesquicarbonate, magnesium carbonate, magnesium bicarbonate, calcium bicarbonate, calcium carbonate, magnesium carbonate hydroxide, and barium carbonate. One or more types of the above may be used.

For example, the multilayer nanofiber sheet 10 can be manufactured according to the following method. First, a nanofiber layer 11 is formed on a surface of a substrate layer 12. The nanofiber layer 11 can be formed by employing electrospinning, for example. Next, a porous layer 13 is layered on a surface of the nanofiber layer 11. Finally, the three layers are fixed together. Fixing methods are as described above. A multilayer nanofiber sheet 10 can be obtained in this way.

To manufacture a multilayer nanofiber sheet 10 with a peelable substrate layer 12, a nanofiber layer 11 is formed on a surface of a substrate layer 12 according to the aforementioned method. In this state, the nanofiber layer 11 and the substrate layer 12 are layered in a peelable state and are not fixed together. Then, a porous layer 13 is layered on a surface of the nanofiber layer 11, and the nanofiber layer 11 and the porous layer 13 are fixed together by one of the aforementioned fixing methods. In the multilayer nanofiber sheet 10 manufactured in this way, the nanofiber layer 11 and the substrate layer 12 are not fixed, whereas the nanofiber layer 11 and the porous layer 13 are fixed together. By configuring the layers of the multilayer nanofiber sheet 10 in this way, the substrate layer 12 can be made peelable.

The invention has been described above according to preferred embodiments thereof, but the scope of the invention is not limited to the foregoing embodiments. For example, the multilayer nanofiber sheet 10 of the foregoing embodiments has a three-layer structure, but instead, at least one of the nanofiber layer 11, the substrate layer 12, and the porous layer 13 may include two or more layers, and the multilayer nanofiber sheet may have a multilayer structure including a total of four or more layers. Further, as described above, other layers may be layered in addition to the nanofiber layer 11, the substrate layer 12, and the porous layer 13, and the multilayer nanofiber sheet may have a multilayer structure including a total of four or more layers.

In relation to the foregoing embodiments, further, the invention also discloses the following multilayer nanofiber sheet and adhesion method for same.

{1}

A multilayer nanofiber sheet comprising:

a nanofiber layer including nanofibers which comprise a water-soluble polymer compound;

a substrate layer arranged on one surface side of the nanofiber layer; and a water-insoluble porous layer arranged on the other surface side of the nanofiber layer, wherein:

the three layers are layered; and the multilayer nanofiber sheet is used in a state in which a surface thereof on the porous layer side is arranged so as to face a surface of an object.

{2}

The multilayer nanofiber sheet as set forth in clause {1}, wherein the porous layer has a thickness of from 3 to 1000 μm.

{3}

The multilayer nanofiber sheet as set forth in clause {1} or {2}, wherein the porous layer is a layer including water-insoluble nanofibers.

{4}

The multilayer nanofiber sheet as set forth in any one of clauses {1} to {3}, wherein the water-soluble polymer compound dissolves by water, and adhesion of the multilayer nanofiber sheet to the object is achieved through the porous layer.

{5}

The multilayer nanofiber sheet as set forth in any one of clauses {1} to {4}, wherein:

one or more types of nanofibers are included in the nanofiber layer; and at least one type of the nanofibers includes a water-soluble polymer compound; and the nanofiber layer is water-soluble as a whole.

{6}

The multilayer nanofiber sheet as set forth in any one of clauses {1} to {5}, wherein in cases where the nanofibers include a water-soluble polymer compound, the nanofibers may further include other components, a first component is included in first nanofibers and a second component is included in second nanofibers, and an acid component and a carbonate are used respectively for the first component and the second component.

{7}

The multilayer nanofiber sheet as set forth in any one of clauses {1} to {6}, wherein the substrate layer is water-insoluble.

{8}

The multilayer nanofiber sheet as set forth in any one of clauses {1} to {7}, wherein:

the substrate layer is in a form of a film or a fiber aggregate, preferably, the substrate layer has low air permeability, and it is preferable that the substrate layer is in the form of a film.

{9}

The multilayer nanofiber sheet as set forth in any one of clauses {1} to {8}, wherein:

the substrate layer is in a form of a film; and the thickness of the substrate layer is preferably 5 µm or greater, more preferably 10 µm or greater, and preferably 500 µm or less, more preferably 300 µm or less, and preferably from 5 to 500 µm, more preferably from 10 to 300 µm.

{10}

The multilayer nanofiber sheet as set forth in any one of clauses {1} to {9}, wherein the substrate layer is in a form of a transparent or translucent film.

{11}

The multilayer nanofiber sheet as set forth in any one of clauses {1} to {10}, wherein:

the porous layer is a layer that is porous and has a multitude of pores; and the pores of the porous layer have an open-cell structure.

{12}

The multilayer nanofiber sheet as set forth in any one of clauses {1} to {11}, wherein the porous layer is a fiber aggregate layer, or a spongy layer having an open-cell structure.

{13}

The multilayer nanofiber sheet as set forth in any one of clauses {1} to {12}, wherein:

the porous layer is made of a fiber aggregate layer;

the fiber aggregate layer is a nonwoven fabric or a mesh sheet; and the nonwoven fabric is a melt-blown nonwoven fabric, a spun-bonded nonwoven fabric, an air-through nonwoven fabric, or a spun-laced nonwoven fabric.

{14}

The multilayer nanofiber sheet as set forth in any one of clauses {1} to {13}, wherein:

the porous layer is made of a fiber aggregate layer;

fibers constituting the fiber aggregate are water-insoluble nanofibers; and the porous layer is constituted by a water-insoluble polymer compound.

{15}

The multilayer nanofiber sheet as set forth in any one of clauses {1} to {14}, wherein:

the water-insoluble polymer compound is a polyolefin resin, a polyethylene terephthalate resin, a polybutylene terephthalate resin, a polylactic acid (PLA), a polyacrylonitrile resin, an acrylic resin such as a polymethacrylate resin, a polystyrene resin, a polyvinyl butyral resin, a polyurethane resin, a polyamide resin, a polyimide resin, or a polyamide imide resin; and the water-insoluble polymer compound may be used singly or two or more types may be used in combination.

{16}

The multilayer nanofiber sheet as set forth in any one of clauses {1} to {15}, wherein the porous layer has the thickness that is preferably 3 µm or greater, more preferably 5 µm or greater, even more preferably 10 µm or greater, is preferably 1000 µm or less, more preferably 500 µm or less, even more preferably 450 µm or less, is preferably from 3 to 1000 µm, more preferably from 5 to 500 µm, even more preferably from 10 to 450 µm.

{17}

The multilayer nanofiber sheet as set forth in any one of clauses {1} to {16}, wherein the three layers are layered in a fixed state.

{18}

The multilayer nanofiber sheet as set forth in clause {17}, wherein the fixed state of the three layers constituting the multilayer nanofiber sheet is maintained (a) before use of the multilayer nanofiber sheet, and (b) after the multilayer nanofiber sheet has been moistened with a liquid substance and the nanofiber layer has dissolved.

{19}

The multilayer nanofiber sheet as set forth in clause {18}, wherein, in the case (b), it is preferable that the substrate layer and the porous layer are fixed together.

{20}

The multilayer nanofiber sheet as set forth in any one of clauses {17} to {19}, wherein fixing of the three layers of the multilayer nanofiber sheet is achieved by adhesion using an adhesive, compression bonding, joining by ultrasonic sealing, laser fusion bonding, or thermal fusion bonding by heat sealing.

{21}

The multilayer nanofiber sheet as set forth in any one of clauses {17} to {20}, wherein a pattern for the fixing is a linear fixing pattern, a dotted fixing pattern, or a fixing pattern which is a combination thereof.

{22}

A multilayer nanofiber sheet adhesion method for making the multilayer nanofiber sheet as set forth in any one of clauses {1} to {21} adhere to a surface of an object, the method comprising bringing a surface of the multilayer nanofiber sheet on the porous layer side into contact with a surface of an object in a state where the multilayer nanofiber sheet's surface on the porous layer side is moistening with a liquid substance, and thus making the multilayer nanofiber sheet's surface adhere to the object's surface.

{23}

A multilayer nanofiber sheet adhesion method for making the multilayer nanofiber sheet as set forth in any one of clauses {1} to {21} adhere to a surface of an object, the method comprising bringing a surface of the multilayer nanofiber sheet on the porous layer into contact with a surface of an object in a state where the object's surface is moistened with a liquid substance, and thus making the multilayer nanofiber sheet's surface adhere to the object's surface.

{24}

A multilayer nanofiber sheet adhesion method for making the multilayer nanofiber sheet as set forth in any one of clauses {1} to {16} adhere to a surface of an object, the method comprising:

bringing a surface of the multilayer nanofiber sheet on the porous layer side into contact with a surface of an object in a state where the multilayer nanofiber sheet's surface on the porous layer side is moistening with a liquid substance, and thus making the multilayer nanofiber sheet's surface adhere to the object's surface; and then peeling off the substrate layer from the nanofiber layer.

{25}

A multilayer nanofiber sheet adhesion method for making the multilayer nanofiber sheet as set forth in any one of clauses {1} to {16} adhere to a surface of an object, the method comprising:

bringing a surface of the multilayer nanofiber sheet on the porous layer into contact with a surface of an object in a state where the object's surface is moistened with a liquid substance, and thus making the multilayer nanofiber sheet's surface adhere to the object's surface; and then peeling off the substrate layer from the nanofiber layer.

{26}

The multilayer nanofiber sheet adhesion method as set forth in any one of clauses {22} to {25}, wherein the liquid substance that is used is water, an aqueous solution, an aqueous dispersion, an emulsion such as an O/W emulsion, or an aqueous liquid thickened by a thickener such as a thickening polysaccharide.

EXAMPLES

The present invention is described in further detail below according to Examples. The scope of the invention, however, is not limited to the Examples. Unless specifically stated otherwise, "%" refers to "% by mass (mass %)".

Example 1

Figure 2:
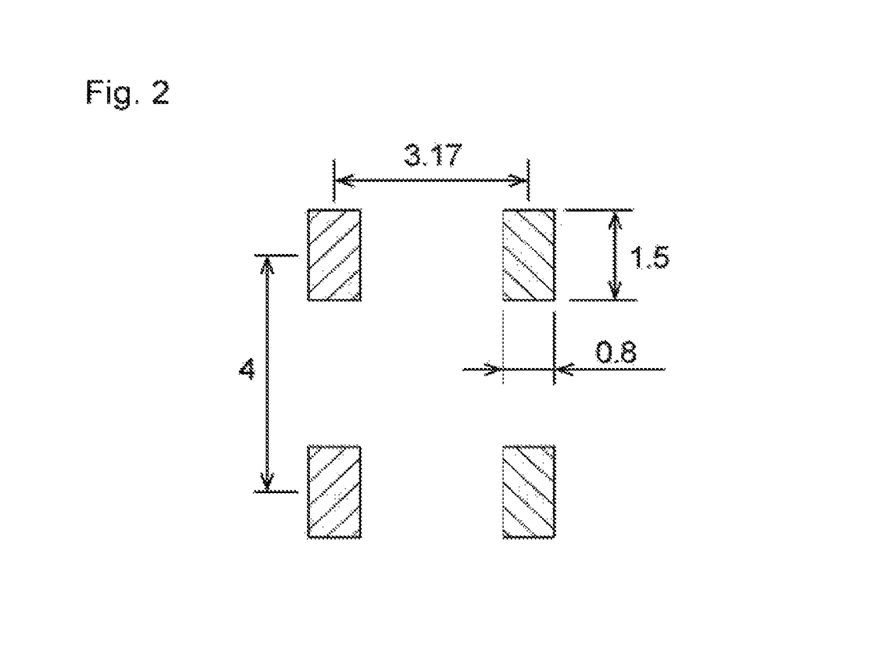
FIG. 2 is a plan view illustrating a joining pattern of ultrasonic seals in a multilayer nanofiber sheet obtained in Example 1.

A multilayer nanofiber sheet having the structure illustrated in FIG. 1 was manufactured. A 25 μm-thick polypropylene (PP) film was used for the substrate layer. A nanofiber layer made of pullulan nanofibers was formed on one surface of the PP film. The thickness of the nanofibers was 600 nm, and the basis weight of the nanofiber layer was 20 g/m$^2$. The nanofiber layer was formed by electrospinning using an aqueous solution including 15% of pullulan and 85% of water. The conditions under which electrospinning was performed were as follows: voltage: 25 kV; distance between electrodes: 200 mm; discharge amount: 1 ml/h. Next, a porous layer was superposed on a surface of the nanofiber layer. For the porous layer, a spun-bonded nonwoven fabric made of polypropylene and having a thickness of 80 μm and a basis weight of 12 g/m$^2$ was used. In this laminate in which these three layers were layered, the layers were fixed together by ultrasonic sealing. Processing positions of the ultrasonic sealing were formed intermittently on the entire surface of the rectangular laminate by employing the pattern illustrated in FIG. 2. The unit employed in the figure is millimeters (mm). In this way, the intended multilayer nanofiber sheet 10 was obtained.

Examples 2 to 4

For the porous layer, the respective nonwoven fabrics described in Table 1 below were used. The fixing method employed was as described in the Table. Other than the above, respective multilayer nanofiber sheets were obtained as in Example 1.

In Example 2, for the porous layer, a spun-bonded nonwoven fabric made of polypropylene and having a thickness of 115 μm and a basis weight of 17 g/m$^2$ was used. In Example 3, for the porous layer, an air-through nonwoven fabric having a thickness of 926 μm and a basis weight of 25 g/m$^2$ was used, the air-through nonwoven fabric being made by blending, at a ratio of 50:50, a core-sheath conjugate fiber (2.0 dtex) including polyethylene terephthalate as the core and polyethylene as the sheath and a core-sheath conjugate fiber (5.6 dtex) including polypropylene as the core and polyethylene as the sheath. In Example 4, for the porous layer, an air-through nonwoven fabric having a thickness of 1660 μm and a basis weight of 25 g/m$^2$ was used, the air-through nonwoven fabric being made of a core-sheath conjugate fiber (2.0 dtex) including polyethylene terephthalate as the core and polyethylene as the sheath. Compression bonding was employed for the fixing method, wherein the three layers, i.e., the porous layer, the nanofiber layer, and the substrate layer, were fixed together by compression bonding by sandwiching the three layers between a no-staple stapler (Harinacs (registered trademark) from Kokuyo Co., Ltd.). Compression bonding was performed at positions along the entire outer periphery of the rectangular laminate.

Example 5

For the porous layer, a mesh sheet (product name Tea Road Sharp 5800F from Yamanaka Industry Co., Ltd.) was used. An adhesive was employed for the fixing method. The adhesive was applied with a spray (product name Spray Glue 55 from Sumitomo 3M Limited) continuously over the entire surface of the rectangular laminate. Other than the above, a multilayer nanofiber sheet was obtained as in Example 1.

Examples 6 and 7

For the porous layer, a nanofiber layer made of polyvinyl butyral (S-LEC (registered trademark) BM-1 from Sekisui Chemical Co., Ltd.) was used. The nanofiber layer was formed by electrospinning by using a solution including 13% of polyvinyl butyral and 87% of ethanol. The conditions under which electrospinning was performed were as follows: voltage: 30 kV; distance between electrodes: 200 mm; discharge amount: 1 ml/h. The thickness of the nanofibers was 450 nm. The thickness of the respective porous layers was as shown in Table 1. Compression bonding was employed for the fixing method. Fixing was performed as in Examples 2 to 4. For the substrate layer, a 20-μm-thick polypropylene film was used. Other than the above, respective multilayer nanofiber sheets were obtained as in Example 1.

Example 8

A multilayer nanofiber sheet was obtained as in Example 6, except that, for the substrate layer, a long-fiber nonwoven fabric made of cupra rayon and having a thickness of 30 µm was used. The thicknesses of the porous layer and the nanofiber layer were as shown in Table 1.

Example 9

A multilayer nanofiber sheet 10 was configured so as to be capable of producing carbon dioxide by including, in the nanofiber layer 11, 5.1% of citric acid as a first component and 4.2% of sodium bicarbonate as a second component. The layers were not fixed together. A multilayer nanofiber sheet was obtained, with the substrate layer and the porous layer configured as in Example 8.

Comparative Example 1

In this Comparative Example, no substrate layer or porous layer was formed in Example 1. Thus, the nanofiber sheet of this Comparative Example was made only of a nanofiber layer.

Comparative Example 2

In this Comparative Example, no porous layer was formed in Example 1. Thus, the nanofiber sheet of this Comparative Example was made only of a nanofiber layer and a substrate layer. The nanofiber sheet was formed by directly spinning and layering nanofibers onto a 60-µm-thick polypropylene film, serving as the substrate layer, by electrostatic spinning. Thus, the nanofiber layer and the substrate layer were layered only by electrostatic force, without later subjecting them to a fixing treatment.

Evaluation:

The handleability, the remaining-liquid amount and feel upon use after peeling of the nanofiber sheet, and the peeling strength of each of the nanofiber sheets obtained according to the Examples and Comparative Examples were evaluated and measured according to the following methods. The results are shown in Table 1 below.

Handleability:

Three male and female panelists between 30 and 45 years old evaluated the handleability of each nanofiber sheet by pinching the sheet with his/her fingers. Each sheet was rated according to the following criteria.

3: The pullulan nanofibers do not dissolve even when various parts of the sheet are pinched, and nothing adheres to the fingers.

2: The pullulan nanofibers in the part pinched with the fingers slightly swell by the moisture of the fingers, and the sheet shape slightly deforms.

1: The pullulan nanofibers in the part pinched with the fingers dissolve and adhere to the fingers.

Feel Upon Use and Remaining-Liquid Amount:

Three male and female panelists (A, B, and C) between 30 and 45 years old evaluated the relationship between the feel upon use and the remaining-liquid amount after peeling of the nanofiber sheet. A surface, on the porous layer side, of a nanofiber sheet cut out into a 20-by-40 mm rectangle was applied with 0.2 g of a commercially available skin lotion A (the composition is shown in Table 2), and the sheet was attached to the cheek such that the porous layer side contacted the skin. After 3 minutes, the nanofiber sheet was peeled off from the cheek, and the feel upon use was evaluated from the viewpoint of the stickiness and moisturized feel of the skin. If the remaining-liquid amount on the skin is too large, the feel upon use deteriorates because a strong stickiness remains on the skin. However, if the remaining-liquid amount is too small, the feel upon use also deteriorates because a moisturized feel cannot be obtained. An extremely small remaining-liquid amount is also not preferable, in terms that the effective components become difficult to supply to the skin. Therefore, the evaluation was performed according to the following criteria. The results are shown in Table 1.

3: Moderate moisturized feel and little stickiness.
2: Somewhat insufficient moisturized feel, or somewhat sticky.
1: No moisturized feel, or very sticky.

The total score for the three panelists was summed up, and each sheet was rated according to the following criteria.

Total score of 9:5.
Total score of 8 or 7:4.
Total score of 6 or 5:3.
Total score of 4:2.
Total score of 3:1.

Remaining-Liquid Amount After Peeling of Nanofiber Sheet:

The following measurement was performed to measure the remaining-liquid amount actually transferred to the skin side. A commercially available skin lotion A (the composition is shown in Table 2) was applied to the surface, on the porous layer side, of each nanofiber sheet (except for Comparative Examples 1 and 2) cut out in a 20-by-40 mm rectangle. As for Comparative Example 1, 0.2 g of the skin lotion was supplied onto a surface of a synthetic resin-made plate having a known mass, and the nanofiber sheet was made to adhere onto the synthetic resin-made plate moistened with the skin lotion. As for Comparative Example 2, the skin lotion was applied to a surface of the substrate layer made of a PP film. A pump was used to supply 0.2 g of the skin lotion. The surface, on the porous layer side, of each nanofiber sheet was made to adhere to a synthetic resin-made plate having a known mass. After 3 minutes, the nanofiber sheet was peeled off from the plate, and the mass of the plate was measured. The value found by subtracting the mass of only the plate from the measured mass was considered the remaining-liquid amount. The percentage (%) of the remaining-liquid amount was calculated based on the percentage of the remaining-liquid amount to the total mass, 0.216 g, of 0.2 g of skin lotion and 0.016 g of pullulan nanofibers in the 20-by-40 mm rectangle (or the total mass of the nanofiber sheet of Comparative Example 1 and the skin lotion).

Peeling Strength:

The surface, on the substrate layer side, of each nanofiber sheet cut out in a 15-mm wide, 100-mm long rectangle was bonded and fixed on a horizontal stage by using a double-faced adhesive tape (Nicetack (product name) from Nichiban Co., Ltd.) that is 15-mm wide and 100-mm long. Measurement is possible if the substrate layer is 30 mm long.

The device used for measuring the peeling strength was a 180° peel tester (Peeling Tester Model IPT200-5N with a measurement range between 0.001 and 5.0 N, from Imada Co., Ltd.). With 1 to 2 mm of an end portion of the nanofiber sheet's porous layer being fixed firmly by a clip attached to a load cell of the peel tester, peeling was performed at a speed of 1,000 mm/min up to a peeling angle (the angle between the nanofiber sheet and the adhesive tape) of from 165 to 180°. The value of the load cell at this time (the peeling strength between the substrate layer and the porous layer) was considered the peeling strength. The greater the value of the peeling strength, the greater the mechanical strength. Each sheet was rated according to the following criteria based on the value of the peeling strength.

5: Peeling strength is 0.5 N or greater.
4: Peeling strength is 0.1 N or greater to less than 0.5 N.
3: Peeling strength is 0.05 N or greater to less than 0.1 N.
2: Peeling strength is 0.01 N or greater to less than 0.05 N.
1: Peeling strength is less than 0.01 N.

TABLE 2

| Skin Lotion A | |
| --- | --- |
| Components | (%) |
| Purified water | 74.35 |
| Glycerin | 10 |
| Dipropylene glycol | 4 |
| 1,3-Propane diol | 4 |
| Polyethylene glycol | 4 |
| Polyoxyethylene glucoside | 1 |
| 2-(2-Hydroxyethoxy)ethyl guanidine succinate | 0.5 |

TABLE 1

| | | Example 1 | Example 2 | Example 3 | Example 4 | Example 5 | Example 6 |
| --- | --- | --- | --- | --- | --- | --- | --- |
| Porous layer | Type | Spun-bonded nonwoven fabric | Spun-bonded nonwoven fabric | Air-through nonwoven fabric | Air-through nonwoven fabric | Mesh sheet (Porosity: 35%) | PVB nanofiber layer |
| | Thickness (μm) | 80 | 115 | 926 | 1660 | 74 | 40 |
| Nanofiber layer | Basis weight (g/m²) | 20 | 20 | 20 | 20 | 20 | 20 |
| Substrate layer | Type | PP film | PP film | PP film | PP film | PP film | PP film |
| | Thickness (μm) | 25 | 25 | 25 | 25 | 25 | 20 |
| Fixing method | | Ultrasonic | Compression bonding | Compression bonding | Compression bonding | Adhesive | Compression bonding |
| Handleability | Evaluation | 5 | 5 | 5 | 5 | 5 | 5 |
| Evaluation of feel upon use and | Panelist A | 3 | 3 | 3 | 1 | 2 | 3 |
| | Panelist B | 3 | 3 | 3 | 1 | 2 | 3 |
| | Panelist C | 3 | 3 | 3 | 1 | 3 | 3 |
| remaining-liquid amount | Total | 9 | 9 | 9 | 3 | 7 | 9 |
| | Evaluation | 5 | 5 | 5 | 1 | 4 | 5 |
| | Remaining-liquid amount (%) | 21 | 21 | 10 | 3 | 32 | 23 |
| Peeling strength | Peeling strength (N) | 0.560 | 0.125 | 0.072 | 0.134 | 0.016 | 0.090 |
| | Evaluation | 5 | 4 | 3 | 4 | 2 | 3 |
| Total evaluation | | 15 | 14 | 13 | 10 | 11 | 13 |

| | | Example 7 | Example 8 | Example 9 | Comparative Example 1 | Comparative Example 2 |
| --- | --- | --- | --- | --- | --- | --- |
| Porous layer | Type | PVB nanofiber layer | PVB nanofiber layer | PVB nanofiber layer | None | None |
| | Thickness (μm) | 3 | 10 | 10 | None | None |
| Nanofiber layer | Basis weight (g/m²) | 20 | 12 | 12 | 20 | 20 |
| Substrate layer | Type | PP film | Nonwoven fabric | Nonwoven fabric | None | PP film |
| | Thickness (μm) | 20 | 30 | 30 | — | 60 |
| Fixing method | | Compression bonding | Compression bonding | None | None | None |
| Handleability | Evaluation | 3 | 5 | 4 | 1 | 1 |
| Evaluation of feel upon use and | Panelist A | 2 | 3 | 2 | 1 | 1 |
| | Panelist B | 2 | 3 | 3 | 1 | 1 |
| | Panelist C | 3 | 3 | 3 | 1 | 1 |
| remaining-liquid amount | Total | 7 | 9 | 8 | 3 | 3 |
| | Evaluation | 4 | 5 | 4 | 1 | 1 |
| | Remaining-liquid amount (%) | 36 | 12 | 14 | 100 | 47 |
| Peeling strength | Peeling strength (N) | 0.052 | 1.548 | 0.049 | — | — |
| | Evaluation | 3 | 5 | 2 | — | — |
| Total evaluation | | 10 | 13 | 10 | 2 | 2 |

TABLE 2-continued

Skin Lotion A

| Components | (%) |
|---|---|
| pH adjuster | 0.15 |
| Xanthan gum | 0.05 |
| Polyoxyethylene octyldodecyl ether | 0.2 |
| Silicone oil | 0.1 |
| Glycerylmonostearate monomyristate | 0.1 |
| Neopentyl glycol dicaprate | 0.1 |
| Squalane | 0.05 |
| Phenoxy ethanol | 0.4 |
| Plant extract liquid | 1 |
| Total | 100 |

The results shown in Table 1 reveal that the nanofiber sheets obtained according to the respective Examples have excellent handleability, high peeling strength, and a moderately small remaining-liquid amount on the skin. In contrast, the results show that the nanofiber sheet of Comparative Example 1, which consists only of a nanofiber layer, is inferior in handleability and also the nanofiber sheet of Comparative Example 2, which does not include a porous layer, is inferior in handleability.

INDUSTRIAL APPLICABILITY

This invention provides a multilayer nanofiber sheet having excellent handleability and high adhesiveness to an object.

The invention claimed is:

1. A multilayer nanofiber sheet comprising:
   a water-soluble nanofiber layer including nanofibers which comprise a water-soluble polymer compound;
   a substrate layer arranged on one surface side of the water-soluble nanofiber layer; and
   a water-insoluble porous layer having a thickness of from 3 to 1000 μm arranged on the other surface side of the water-soluble nanofiber layer, the porous layer having a multitude of pores, the pores of the porous layer have an open-cell structure,
   wherein:
   the three layers are layered;
   the multilayer nanofiber sheet is used in a state in which a surface thereof on the porous layer side is arranged so as to face a surface of an object; and
   the water-soluble polymer compound is pullulan, mucopolysaccharide, pectin, xylan, lignin, glucomannan, galacturonic acid, *psyllium* seed gum, tamarind seed gum, gum arabic, tragacanth gum, water-soluble soybean polysaccharides, alginic acid, carrageenan, laminaran, agar (agarose), fucoidan, or methyl cellulose that dissolves by water, and
   adhesion of the multilayer nanofiber sheet to the object is achieved as the water-soluble polymer dissolves and penetrates through the water-insoluble porous layer, by moistening the multilayer nanofiber sheet with a lotion, thereby allowing the nanofiber sheet to adhere to the surface of the object;
   wherein the water-soluble nanofiber layer and the water-insoluble porous layer are in direct contact with one another;
   wherein the outer surface of the water-insoluble porous layer constitutes an outer surface of the multilayer nanofiber sheet;
   wherein the substrate layer is water-insoluble; and
   wherein a value of the air permeability of the substrate layer in air resistance is 30 s/100 ml or greater.

2. The multilayer nanofiber sheet according to claim 1, wherein the porous layer is a layer including water-insoluble nanofibers.

3. The multilayer nanofiber sheet according to claim 1, wherein: one or more types of nanofibers are included in the water-soluble nanofiber layer; and at least one type of the nanofibers includes a water-soluble polymer compound; and the water-soluble nanofiber layer is water-soluble as a whole.

4. The multilayer nanofiber sheet according to claim 1, wherein the substrate layer is water-insoluble.

5. The multilayer nanofiber sheet according to claim 1, wherein the substrate layer is in a form of a film or a fiber aggregate.

6. The multilayer nanofiber sheet according to claim 1, wherein the substrate layer is in a form of a transparent or translucent film.

7. The multilayer nanofiber sheet according to claim 1, wherein the porous layer is a fiber aggregate layer, or a spongy layer having an open-cell structure.

8. The multilayer nanofiber sheet according to claim 1, wherein: the porous layer is made of a fiber aggregate layer; fibers constituting the fiber aggregate are water-insoluble nanofibers; and the porous layer is constituted by a water-insoluble polymer compound.

9. The multilayer nanofiber sheet according to claim 1, wherein the three layers are layered in a fixed state.

10. The multilayer nanofiber sheet according to claim 9, wherein fixing of the three layers of the multilayer nanofiber sheet is achieved by adhesion using an adhesive, compression bonding, joining by ultrasonic sealing, laser fusion bonding, or thermal fusion bonding by heat sealing.

11. The multilayer nanofiber sheet according to claim 1, wherein, in the case (b), the substrate layer and the porous layer are fixed together.

12. A multilayer nanofiber sheet comprising:
   a water-soluble nanofiber layer including nanofibers which comprise a water-soluble polymer compound; is pullulan, mucopolysaccharide, pectin, xylan, lignin, glucomannan, galacturonic acid, *psyllium* seed gum, tamarind seed gum, gum arabic, tragacanth gum, water-soluble soybean polysaccharides, alginic acid, carrageenan, laminaran, agar (agarose), fucoidan, or methyl cellulose,
   a substrate layer arranged on one surface side of the water-soluble nanofiber layer; and
   a water-insoluble porous layer having a thickness of from 3 to 1000 μm arranged on the other surface side of the water-soluble nanofiber layer, the porous layer having a multitude of pores, the pores of the porous layer have an open-cell structure,
   wherein:
   the three layers are layered;
   the multilayer nanofiber sheet is used in a state in which a surface thereof on the porous layer side is arranged so as to face a surface of an object; and
   the fixed state of the three layers constituting the multilayer nanofiber sheet is maintained (a) before use of the multilayer nanofiber sheet, and (b) after the multilayer nanofiber sheet has been moistened with a lotion and the water-soluble nanofiber layer has dissolved;

wherein a basis weight of the water-soluble nanofiber layer is 100 g/m² or less; and wherein a lotion is applied on the multilayer nanofiber sheet in an amount of 0.2 g/800 mm² or greater.

13. The multilayer nanofiber sheet according to claim 12, wherein the water-soluble nanofiber layer and the water-insoluble porous layer are in direct contact with one another;

wherein the outer surface of the water-insoluble porous layer constitutes an outer surface of the multilayer nanofiber sheet;

wherein the substrate layer is water-insoluble; and wherein a value of the air permeability of the substrate layer in air resistance is 30 s/100 ml or greater.

14. A multilayer nanofiber sheet comprising:

wherein the multilayer nanofiber sheet comprises: a water-soluble nanofiber layer including nanofibers which comprise a water-soluble polymer compound, is pullulan, mucopolysaccharide, pectin, xylan, lignin, glucomannan, galacturonic acid, *psyllium* seed gum, tamarind seed gum, gum arabic, tragacanth gum, water-soluble soybean polysaccharides, alginic acid, carrageenan, laminaran, agar (agarose), fucoidan, or methyl cellulose, a substrate layer arranged on one surface side of the water-soluble nanofiber layer, and a water-insoluble porous layer having a thickness of from 3 to 1000 μm arranged on the other surface side of the water-soluble nanofiber layer, wherein: the three layers are layered, and the multilayer nanofiber sheet is used in a state in which a surface thereof on the porous layer side is arranged so as to face a surface of an object, and whereupon, bringing a surface of the multilayer nanofiber sheet on the porous layer side into contact with a surface of an object in a state where the multilayer nanofiber sheet's surface on the porous layer side is moistened with a liquid substance, the multilayer nanofiber sheet's surface adheres to the object's surface as the water-soluble polymer dissolves and penetrates through the water-insoluble porous layer, thereby allowing the nanofiber sheet to adhere to the surface of the object;

OR wherein the multilayer nanofiber sheet comprises: a water-soluble nanofiber layer including nanofibers which comprise a water-soluble polymer compound, is pullulan, mucopolysaccharide, pectin, xylan, lignin, glucomannan, galacturonic acid, *psyllium* seed gum, tamarind seed gum, gum arabic, tragacanth gum, water-soluble soybean polysaccharides, alginic acid, carrageenan, laminaran, agar (agarose), fucoidan, or methyl cellulose, a substrate layer arranged on one surface side of the water-soluble nanofiber layer, and a water-insoluble porous layer having a thickness of from 3 to 1000 μm arranged on the other surface side of the water-soluble nanofiber layer, wherein: the three layers are layered, and the multilayer nanofiber sheet is used in a state in which a surface thereof on the porous layer side is arranged so as to face a surface of an object, and whereupon, bringing a surface of the multilayer nanofiber sheet on the porous layer side into contact with a surface of an object in a state where the object's surface is moistened with a lotion, the multilayer nanofiber sheet's surface adheres to the object's surface as the water-soluble polymer dissolves and penetrates through the water-insoluble porous layer, thereby allowing the nanofiber sheet to adhere to the surface of the object;

wherein a basis weight of the water-soluble nanofiber layer is 100 g/m² or less; and wherein a lotion is applied on the multilayer nanofiber sheet in an amount of 0.2 g/800 mm² or greater.

15. The multilayer nanofiber sheet according to claim 14, wherein:

the substrate layer is peelable from the water-soluble nanofiber layer, and whereupon, bringing a surface of the multilayer nanofiber sheet on the porous layer side into contact with a surface of an object in a state where the multilayer nanofiber sheet's surface on the porous layer side is moistened with a lotion, the multilayer nanofiber sheet's surface adheres to the object's surface as the water-soluble polymer dissolves and penetrates through the water-insoluble porous layer, thereby allowing the nanofiber sheet to adhere to the surface of the object, or whereupon, bringing a surface of the multilayer nanofiber sheet on the porous layer side into contact with a surface of an object in a state where the object's surface is moistened with a lotion, the multilayer nanofiber sheet's surface adheres to the object's surface as the water-soluble polymer dissolves and penetrates through the water-insoluble porous layer, thereby allowing the nanofiber sheet to adhere to the surface of the object;

OR wherein:

the substrate layer is peelable from the water-soluble nanofiber layer, and whereupon, bringing a surface of the multilayer nanofiber sheet on the porous layer side into contact with a surface of an object in a state where the multilayer nanofiber sheet's surface on the porous layer side is moistened with a lotion, the multilayer nanofiber sheet's surface adheres to the object's surface as the water-soluble polymer dissolves and penetrates through the water-insoluble porous layer, thereby allowing the nanofiber sheet to adhere to the surface of the object, while preventing excessive solution from being supplied to the surface of the object in order to promote a comfortable feel, or whereupon, bringing a surface of the multilayer nanofiber sheet on the porous layer side into contact with a surface of an object in a state where the object's surface is moistened with a lotion, the multilayer nanofiber sheet's surface adheres to the object's surface as the water-soluble polymer dissolves and penetrates through the water-insoluble porous layer, thereby allowing the nanofiber sheet to adhere to the surface of the object, while preventing excessive solution from being supplied to the surface of the object in order to promote a comfortable feel.

16. The multilayer nanofiber sheet according to claim 14, wherein the water-soluble nanofiber layer and the water-insoluble porous layer are in direct contact with one another;

wherein the outer surface of the water-insoluble porous layer constitutes an outer surface of the multilayer nanofiber sheet;

wherein the substrate layer is water-insoluble; and wherein a value of the air permeability of the substrate layer in air resistance is 30 s/100 ml or greater.

17. A multilayer nanofiber sheet comprising:
wherein the multilayer nanofiber sheet comprises: a water-soluble nanofiber layer including nanofibers which comprise a water-soluble polymer compound, is pullulan, mucopolysaccharide, pectin, xylan, lignin, glucomannan, galacturonic acid, *psyllium* seed gum, tamarind seed gum, gum arabic, tragacanth gum, water-soluble soybean polysaccharides, alginic acid, carrageenan, laminaran, agar (agarose), fucoidan, or methyl cellulose, a substrate layer arranged on one surface side of the water-soluble nanofiber layer, and a water-insoluble porous layer having a thickness of from 3 to 1000 μm arranged on the other surface side of the water-soluble nanofiber layer,
wherein: the three layers are layered, and the multilayer nanofiber sheet is used in a state in which a surface thereof on the porous layer side is arranged so as to face a surface of an object; and
whereupon, bringing a surface of the multilayer nanofiber sheet on the porous layer side into contact with a surface of an object in a state where the multilayer nanofiber sheet's surface on the porous layer side is moistened with a lotion, the multilayer nanofiber sheet's surface adheres to the object's surface as the water-soluble polymer dissolves and penetrates through the water-insoluble porous layer, thereby allowing the nanofiber sheet to adhere to the surface of the object, and
wherein the fixed state of the three layers constituting the multilayer nanofiber sheet is maintained (a) before use of the multilayer nanofiber sheet, and (b) after the multilayer nanofiber sheet has been moistened with a lotion and the water-soluble nanofiber layer has dissolved;
OR
wherein the multilayer nanofiber sheet comprises: a water-soluble nanofiber layer including nanofibers which comprise a water-soluble polymer compound, is pullulan, mucopolysaccharide, pectin, xylan, lignin, glucomannan, galacturonic acid, *psyllium* seed gum, tamarind seed gum, gum arabic, tragacanth gum, water-soluble soybean polysaccharides, alginic acid, carrageenan, laminaran, agar (agarose), fucoidan, or methyl cellulose, a substrate layer arranged on one surface side of the water-soluble nanofiber layer, and a water-insoluble porous layer having a thickness of from 3 to 1000 μm arranged on the other surface side of the water-soluble nanofiber layer,
wherein: the three layers are layered, and the multilayer nanofiber sheet is used in a state in which a surface thereof on the porous layer side is arranged so as to face a surface of an object, and
whereupon, bringing a surface of the multilayer nanofiber sheet on the porous layer side into contact with a surface of an object in a state where the object's surface is moistened with a lotion, the multilayer nanofiber sheet's surface adheres to the object's surface as the water-soluble polymer dissolves and penetrates through the water-insoluble porous layer, thereby allowing the nanofiber sheet to adhere to the surface of the object, and
wherein the fixed state of the three layers constituting the multilayer nanofiber sheet is maintained (a) before use of the multilayer nanofiber sheet, and (b) after the multilayer nanofiber sheet has been moistened with a lotion and the water-soluble nanofiber layer has dissolved, wherein a basis weight of the water-soluble nanofiber layer is 100 g/m$^2$ or less; and
wherein a liquid substance is applied on the multilayer nanofiber sheet in an amount of 0.2 g/800 mm$^2$ or greater.

18. The multilayer nanofiber sheet according to claim 17,
wherein the water-soluble nanofiber layer and the water-insoluble porous layer are in direct contact with one another;
wherein the outer surface of the water-insoluble porous layer constitutes an outer surface of the multilayer nanofiber sheet;
wherein the substrate layer is water-insoluble; and
wherein a value of the air permeability of the substrate layer in air resistance is 30 s/100 ml or greater.

19. A multilayer nanofiber sheet comprising:
wherein the multilayer nanofiber sheet comprises: a water-soluble nanofiber layer including nanofibers which comprise a water-soluble polymer compound, is pullulan, mucopolysaccharide, pectin, xylan, lignin, glucomannan, galacturonic acid, *psyllium* seed gum, tamarind seed gum, gum arabic, tragacanth gum, water-soluble soybean polysaccharides, alginic acid, carrageenan, laminaran, agar (agarose), fucoidan, or methyl cellulose, a substrate layer arranged on one surface side of the water-soluble nanofiber layer, and a water-insoluble porous layer having a thickness of from 3 to 1000 μm arranged on the other surface side of the water-soluble nanofiber layer,
wherein: the three layers are layered, and the multilayer nanofiber sheet is used in a state in which a surface thereof on the porous layer side is arranged so as to face a surface of an object, and
whereupon, bringing a surface of the multilayer nanofiber sheet on the porous layer side into contact with a surface of an object in a state where the multilayer nanofiber sheet's surface on the porous layer side is moistened with a lotion, the multilayer nanofiber sheet's surface adheres to the object's surface as the water-soluble polymer dissolves and penetrates through the water-insoluble porous layer, thereby allowing the nanofiber sheet to adhere to the surface of the object, while preventing excessive solution from being supplied to the surface of the object in order to promote a comfortable feel;
OR
wherein the multilayer nanofiber sheet comprises: a water-soluble nanofiber layer including nanofibers which comprise a water-soluble polymer compound, is pullulan, mucopolysaccharide, pectin, xylan, lignin, glucomannan, galacturonic acid, *psyllium* seed gum, tamarind seed gum, gum arabic, tragacanth gum, water-soluble soybean polysaccharides, alginic acid, carrageenan, laminaran, agar (agarose), fucoidan, or methyl cellulose, a substrate layer arranged on one surface side of the water-soluble nanofiber layer, and a water-insoluble porous layer having a thickness of from 3 to 1000 μm arranged on the other surface side of the water-soluble nanofiber layer,
wherein: the three layers are layered, and the multilayer nanofiber sheet is used in a state in which a surface thereof on the porous layer side is arranged so as to face a surface of an object, and
whereupon, bringing a surface of the multilayer nanofiber sheet on the porous layer side into contact with a surface of an object in a state where the object's surface is moistened with a lotion, the multilayer nanofiber sheet's surface adheres to the object's surface as the water-soluble polymer dissolves and penetrates through the water-insoluble porous layer, thereby allowing the nanofiber sheet to adhere to the surface of the object, while preventing excessive solution from being supplied to the surface of the object in order to promote a comfortable feel;

wherein a basis weight of the water-soluble nanofiber layer is 100 g/m$^2$ or less; and wherein a lotion is applied on the multilayer nanofiber sheet in an amount of 0.2 g/800 mm$^2$ or greater.

20. The multilayer nanofiber sheet according to claim 19, wherein the water-soluble nanofiber layer and the water-insoluble porous layer are in direct contact with one another;

wherein the outer surface of the water-insoluble porous layer constitutes an outer surface of the multilayer nanofiber sheet;

wherein the substrate layer is water-insoluble; and wherein a value of the air permeability of the substrate layer in air resistance is 30 s/100 ml or greater.

\* \* \* \* \*